United States Patent
Allen et al.

(10) Patent No.: US 12,361,552 B2
(45) Date of Patent: *Jul. 15, 2025

(54) VALIDATING A SAMPLE COLLECTION DEVICE

(71) Applicant: Everly Well, Inc., Austin, TX (US)

(72) Inventors: Christopher Wesley Allen, Austin, TX (US); Claudia Carrillo Gomez, Mexico City (MX); Emma Todd LaPorte, Philadelphia, PA (US); Matthew William Meyer, Cary, NC (US); Nini Luyuan Nathan, Providence, RI (US); Nicholas Mattsson Parker, Austin, TX (US); Jason Michael Pepas, Dripping Springs, TX (US); James Joseph Vanaria, Chicago, IL (US)

(73) Assignee: Everly Well, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/415,420

(22) Filed: Jan. 17, 2024

(65) Prior Publication Data
US 2024/0169529 A1   May 23, 2024

Related U.S. Application Data

(63) Continuation of application No. 18/211,143, filed on Jun. 16, 2023, now Pat. No. 11,915,423.
(Continued)

(51) Int. Cl.
G16H 10/40   (2018.01)
A61B 5/15    (2006.01)
(Continued)

(52) U.S. Cl.
CPC ...... *G06T 7/0012* (2013.01); *A61B 5/150786* (2013.01); *A61B 5/150824* (2013.01); *G06T 7/90* (2017.01); *G16H 10/40* (2018.01); *G06T 2207/10024* (2013.01); *G06T 2207/30242* (2013.01)

(58) Field of Classification Search
CPC .............. G06T 7/0012; G06T 7/90; G06T 2207/10024; G06T 2207/30242; A61B 5/150786; A61B 5/150824; G16H 10/40; G16H 30/20; G16H 30/40; G16H 40/63; G16H 40/67
See application file for complete search history.

(56) References Cited

U.S. PATENT DOCUMENTS

2015/0294460 A1* 10/2015 Satish ............... G06T 7/0012
                                                    382/128
2017/0045729 A1   2/2017 Morrison
(Continued)

OTHER PUBLICATIONS

Fars Esmat Samann: "Real-time Liquid Level and color Detection system using Image Processing"; Dec. 21, 2018; Academic Journal of Nawroz University, pp. 223-227. (Year: 2018).*

*Primary Examiner* — Siamak Harandi
(74) *Attorney, Agent, or Firm* — Van Pelt, Yi & James LLP

(57) ABSTRACT

An image of a sample collection device is captured. The image of the sample collection device is analyzed to determine whether the sample collection device includes a sufficient amount of fluid sample. The image of the sample collection device is validated based on a result of the image analysis.

34 Claims, 17 Drawing Sheets

Related U.S. Application Data

(60) Provisional application No. 63/427,571, filed on Nov. 23, 2022.

(51) Int. Cl.
 *G06T 7/00* (2017.01)
 *G06T 7/90* (2017.01)

(56) References Cited

U.S. PATENT DOCUMENTS

2018/0047192 A1* 2/2018 Kristal ............... G06T 11/60
2020/0211697 A1* 7/2020 Adiri .................. G06T 7/90

* cited by examiner

VALIDATING A SAMPLE COLLECTION DEVICE

CROSS REFERENCE TO OTHER APPLICATIONS

This application is a continuation of U.S. patent application Ser. No. 18/211,143 entitled VALIDATING A SAMPLE COLLECTION DEVICE filed Jun. 16, 2023, which claims priority to U.S. Provisional Patent Application No. 63/427,571 entitled VALIDATING A SAMPLE COLLECTION DEVICE filed Nov. 23, 2022, each of which is incorporated herein by reference for all purposes.

BACKGROUND OF THE INVENTION

A user may utilize an at-home test kit to perform various tests, such as a food sensitivity test, a food allergy test, a celiac disease screening test, a metabolism test, a sexually transmitted disease test, etc. The at-home test kit includes a sample collection device. The user may be required to provide a plurality of blood samples on the sample collection device. Subsequently, the user sends the sample collection device with the plurality of blood samples to a processing facility. At a later date, the user receives a result of performing the at-home test kit. However, in some instances, the user receives a "Quality Not Sufficient" test result because the user did not provide a sufficient amount of blood on the sample collection device. The provider associated with the at-home test kit may provide an additional at-home test kit to the user (e.g., via the mail or other delivery service). The user may use the additional at-home test kit and repeat the above process to obtain an additional test result, but the user needs to wait an additional amount of time before obtaining the additional test result.

BRIEF DESCRIPTION OF THE DRAWINGS

Various embodiments of the invention are disclosed in the following detailed description and the accompanying drawings.

DETAILED DESCRIPTION

Figure 1:
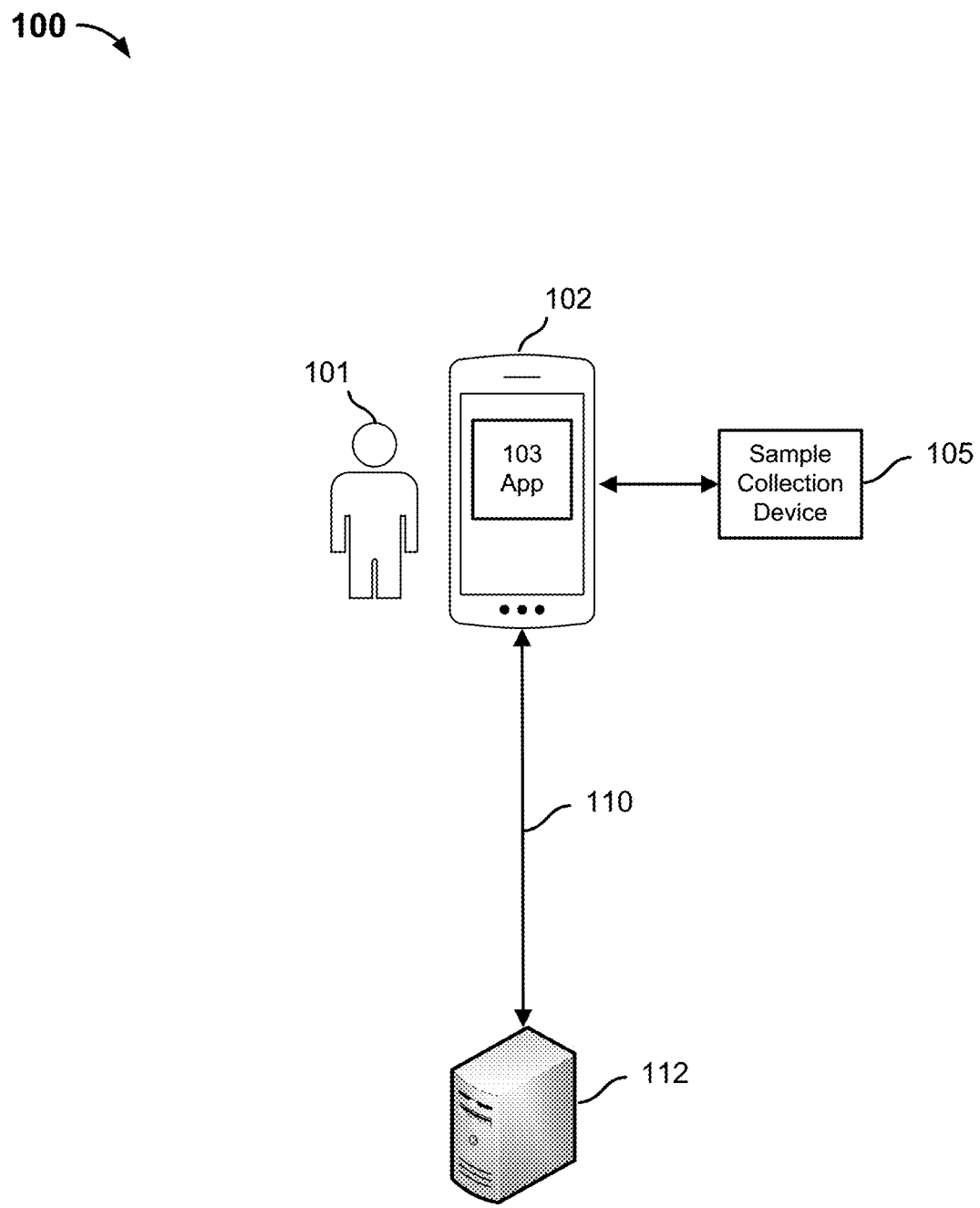
FIG. 1 is a block diagram illustrating an embodiment of a system for validating sample collection devices.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A technique to validate a sample collection device is disclosed herein. The disclosed technique may reduce the amount of time before a user receives a valid test result because the user will be notified of an invalid sample collection device (e.g., "Quality Not Sufficient" test result) before the user provides the sample collection device to a processing facility. The disclosed technique may also reduce the number of resources (e.g., time and lab equipment) used by the processing facility to process invalid sample collection devices because the invalid sample collection devices will be identified before they are provided to the processing facility. In some embodiments, an additional sample collection device is provided with the at-home test kit. A user may perform a second test using the additional sample collection device to obtain a sufficient amount of blood on the additional sample collection device and provide the valid sample collection device to the processing facility for processing.

A user utilizes an electronic device to validate a sample collection device. The electronic device may be a smart phone, a tablet, a laptop, a desktop, a server, a smart device, a cell phone, a mobile device, or any other electronic device that includes a camera. The camera includes an image sensor. The image sensor may be a charge-coupled device (CCD), an active-pixel sensor (CMOS), or any other type of image sensor.

Figure 7:
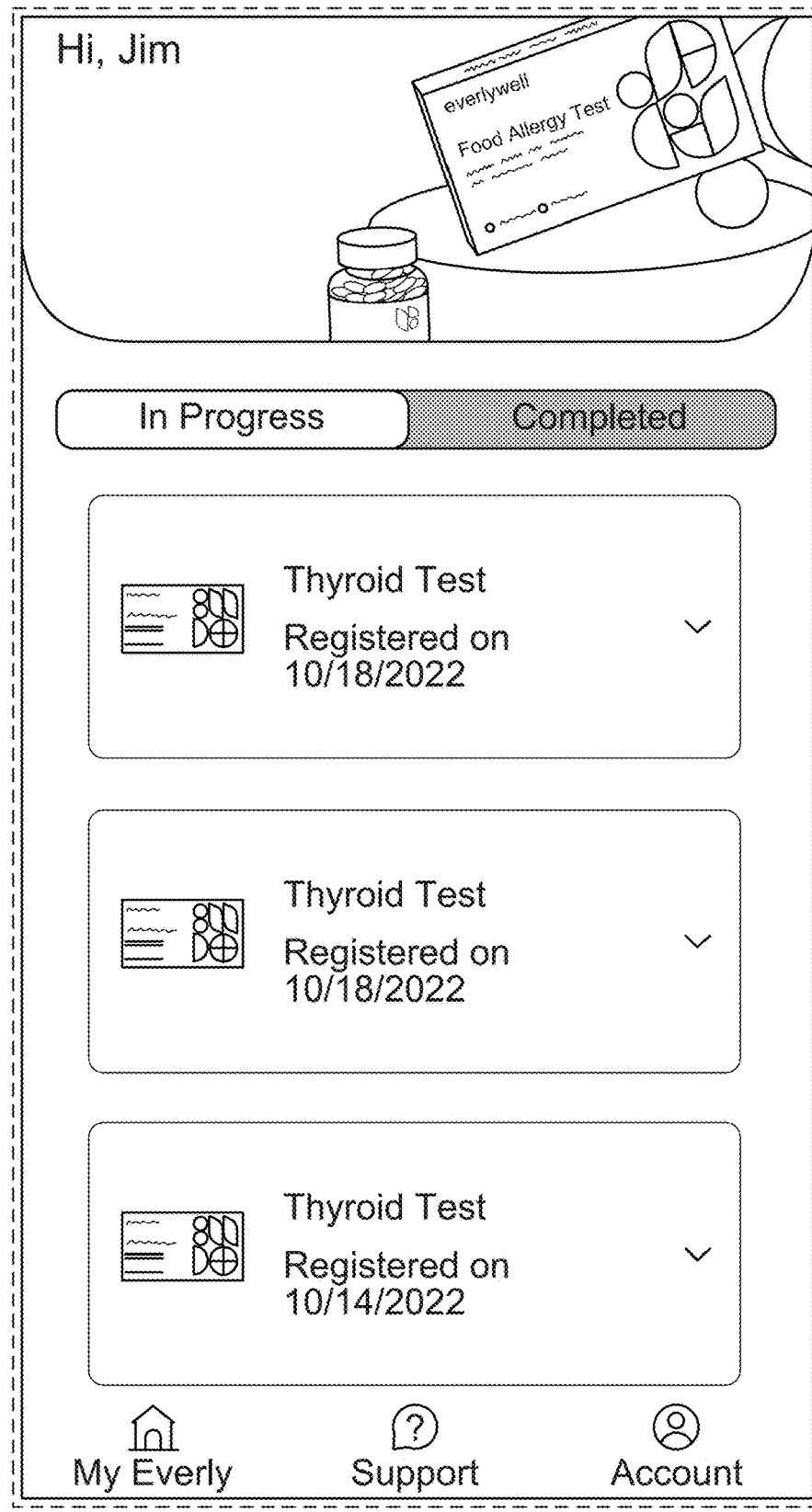
FIG. 7 illustrates a display showing different tests registered to a user in accordance with some embodiments.
Figure 8:
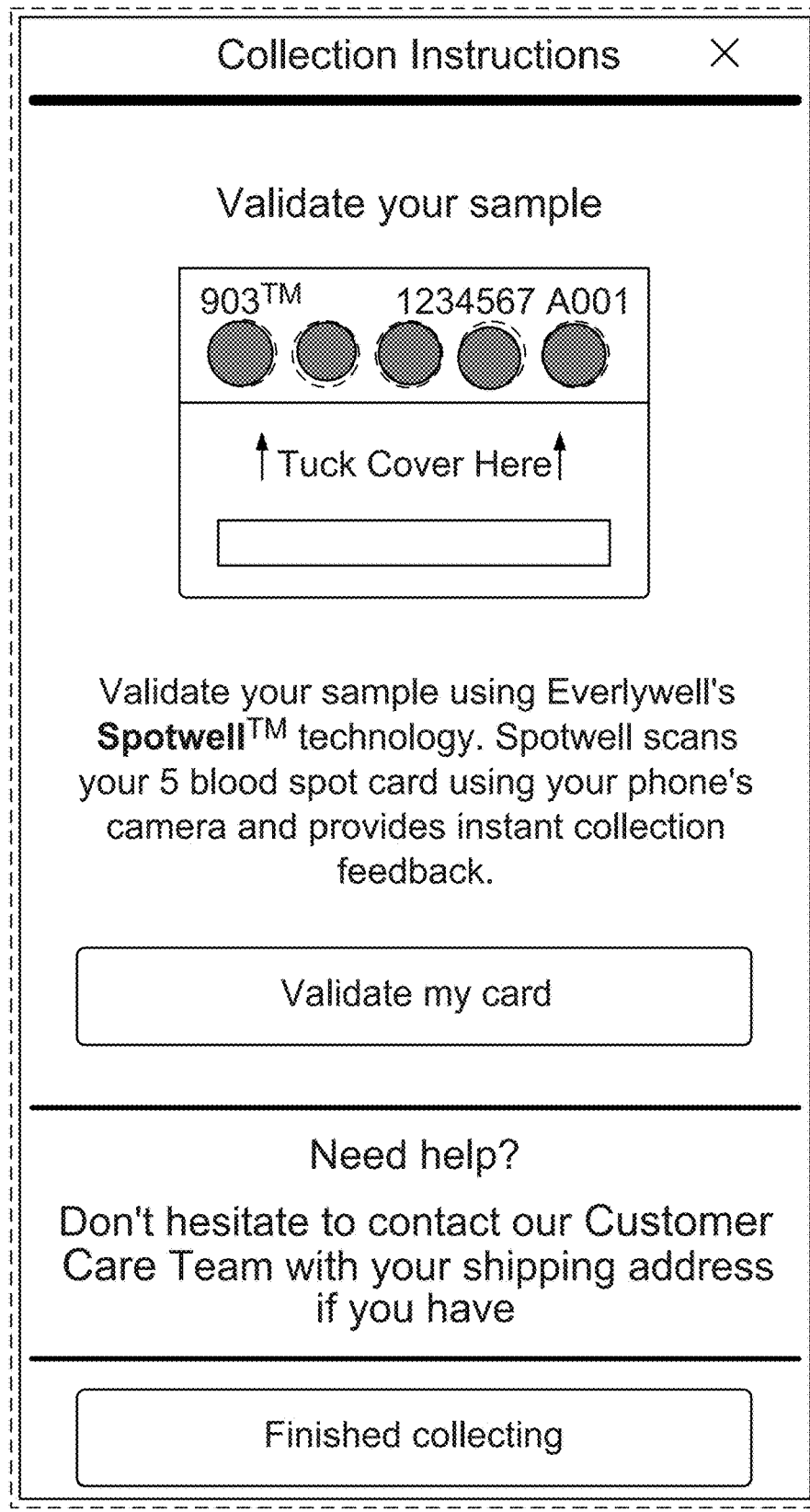
FIG. 8 illustrates an example of validation instructions provided to a user in accordance with some embodiments.
Figure 9:
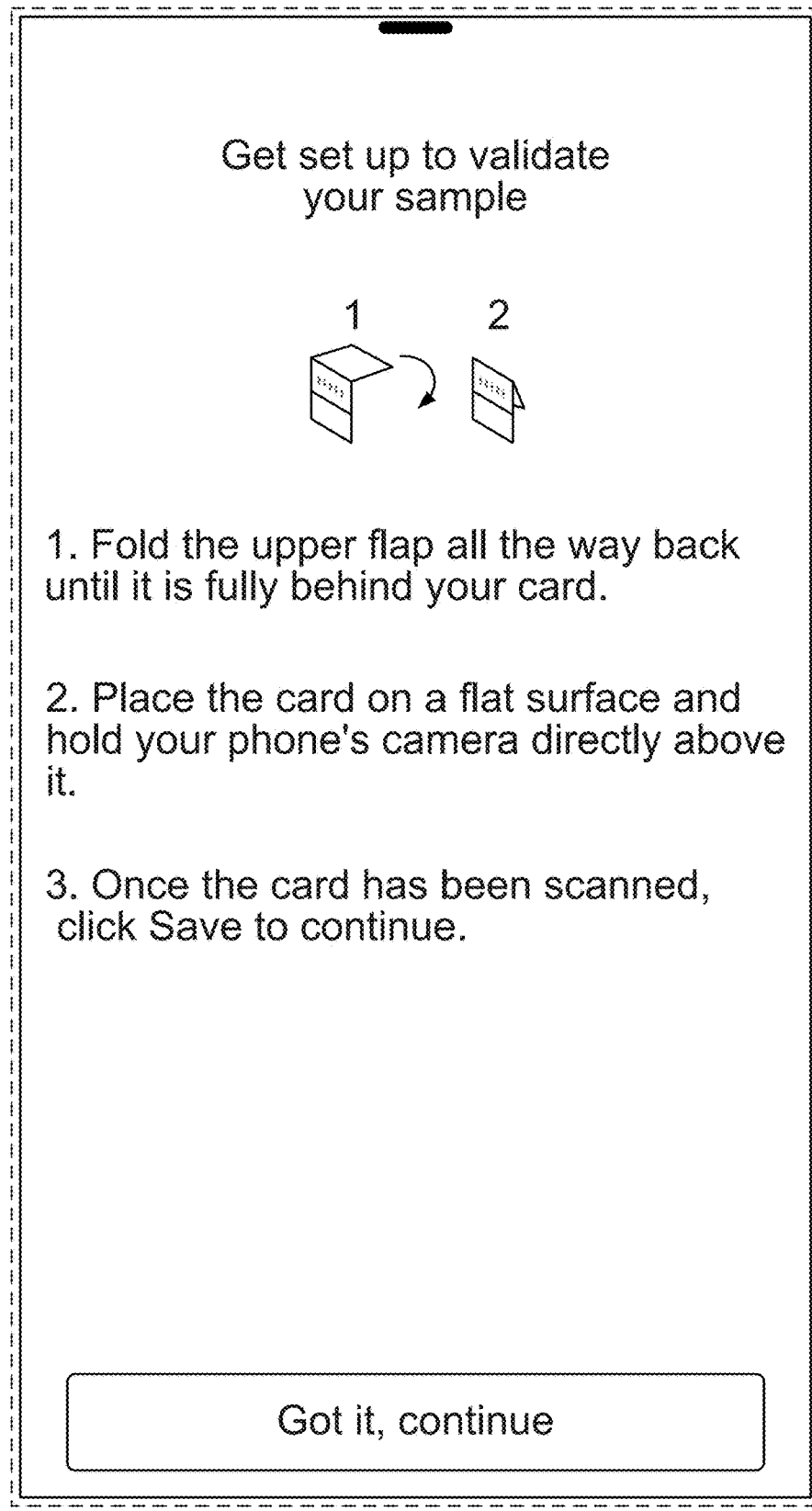
FIG. 9 illustrates an example of validation instructions provided to a user in accordance with some embodiments.

The electronic device includes a test validation application. The test validation application may display to the user one or more test kits associated with the user via a display associated with the electronic device. For example, FIG. 7 illustrates a display 700 showing three different tests registered to a user named "Jim." The test validation application receives a selection of a test kit. In response to receiving the selection, the test validation application provides to the user instructions describing how to validate a sample collection device included in the test kit. The instructions may indicate that the user should utilize the camera associated with the electronic device to capture an image of a used sample collection device (e.g., the sample collection device includes one or more fluid samples associated with the user, a collection cassette, a collection card, etc.). A fluid sample may be a blood sample, a urine sample, a saliva solution, or other body fluid sample. FIG. 8 illustrates an example of a display 800 displaying validation instructions to a user. FIG. 9 illustrates an example of a display 900 displaying validation instructions to a user. The validation instructions may provide instructions describing how the sample collection device is to be folded by the user.

Figure 10:
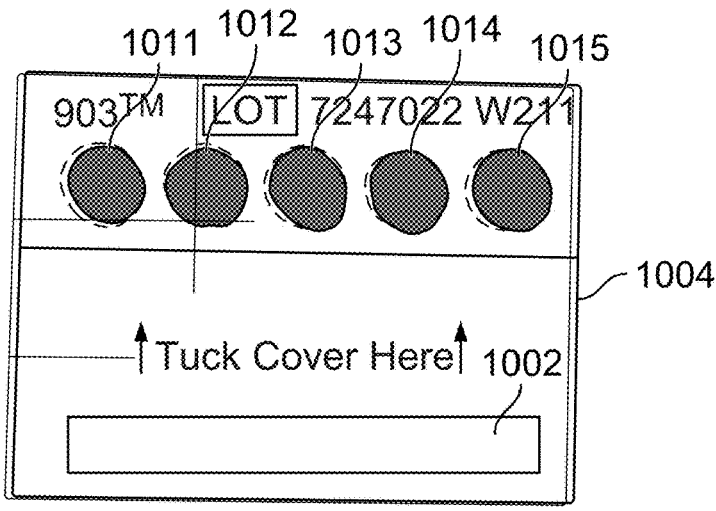
FIG. 10 illustrates an example of an image of a used sample collection device captured by a camera associated with an electronic device in accordance with some embodiments.
Figure 12:
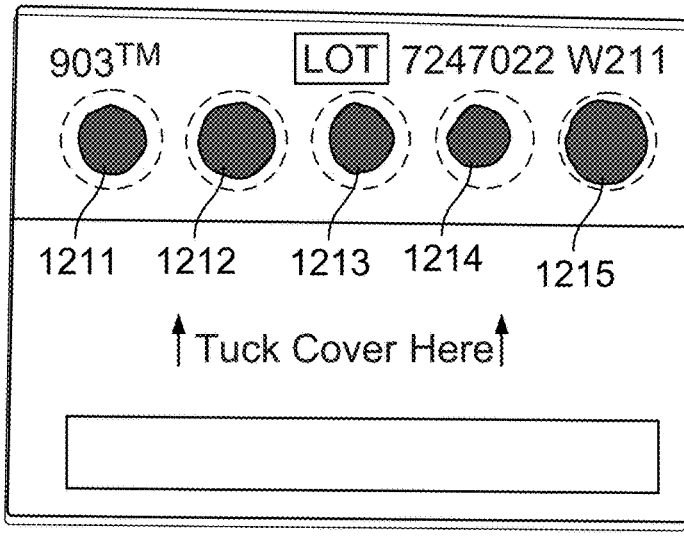
FIG. 12 illustrates an example of an image of a used sample collection device captured by a camera associated with an electronic device in accordance with some embodiments.
Figure 12:
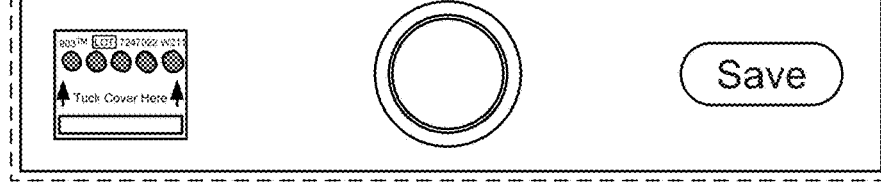
Figure 16:
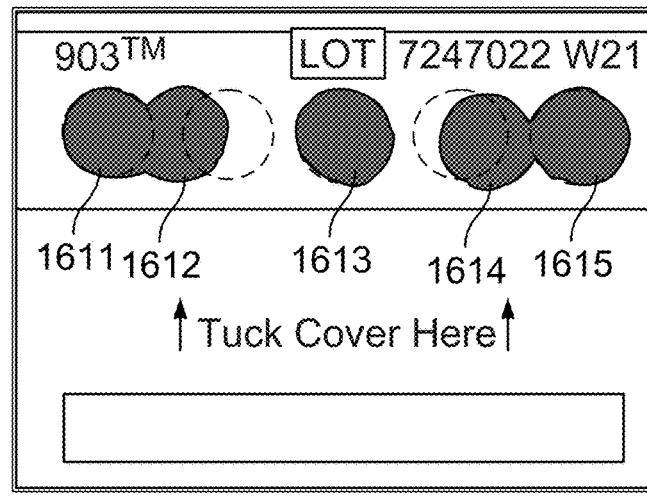
FIG. 16 illustrates an example of an image of a used sample collection device captured by a camera associated with an electronic device in accordance with some embodiments.
Figure 16:
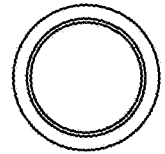

The camera associated with the electronic device captures an image of the used sample collection device. In some embodiments, the test validation application determines whether the image includes the sample collection device. In some embodiments, the image is deemed not to include the sample collection device (e.g., the device is unable to determine whether the image includes the sample collection device because the image is blurry, an insufficient potion of the sample collection device is visible in the image, etc.). In response to a determination that the image is deemed not to include the sample collection device, the test validation application requests the user to capture an additional image. In response to a determination that the image includes the sample collection device, the test validation application analyzes the image utilizing one or more image analysis algorithms to determine whether the sample collection device includes a sufficient amount of fluid sample. FIGS. 10, 12, and 16 illustrate examples of captured images that were analyzed by the test validation application.

The test validation application includes a plurality of image analysis algorithms to validate the sample collection device. The test validation application may serially utilize the plurality of image analysis algorithms to validate the sample collection device. A sample collection device is validated in response to a determination that the user has provided a sufficient amount of fluid to the sample collection device for later analysis at the processing facility. In some embodiments, the test validation application validates the sample collection device after applying a first algorithm of the plurality of image analysis algorithms to the image of the sample collection device. In some embodiments, the test validation application validates the sample collection device after applying at least two of the plurality of image analysis algorithms to the image of the sample collection device. For example, the used sample collection devices of FIGS. 11 and 17 have been validated because there is a sufficient amount of blood. In response to validating the used sample collection device, the test validation application may provide a notification to the user via the display associated with the electronic device. The notification may indicate that the used sample collection device has been validated (e.g., approved) and further handling instructions for the used sample collection device.

Figure 13:
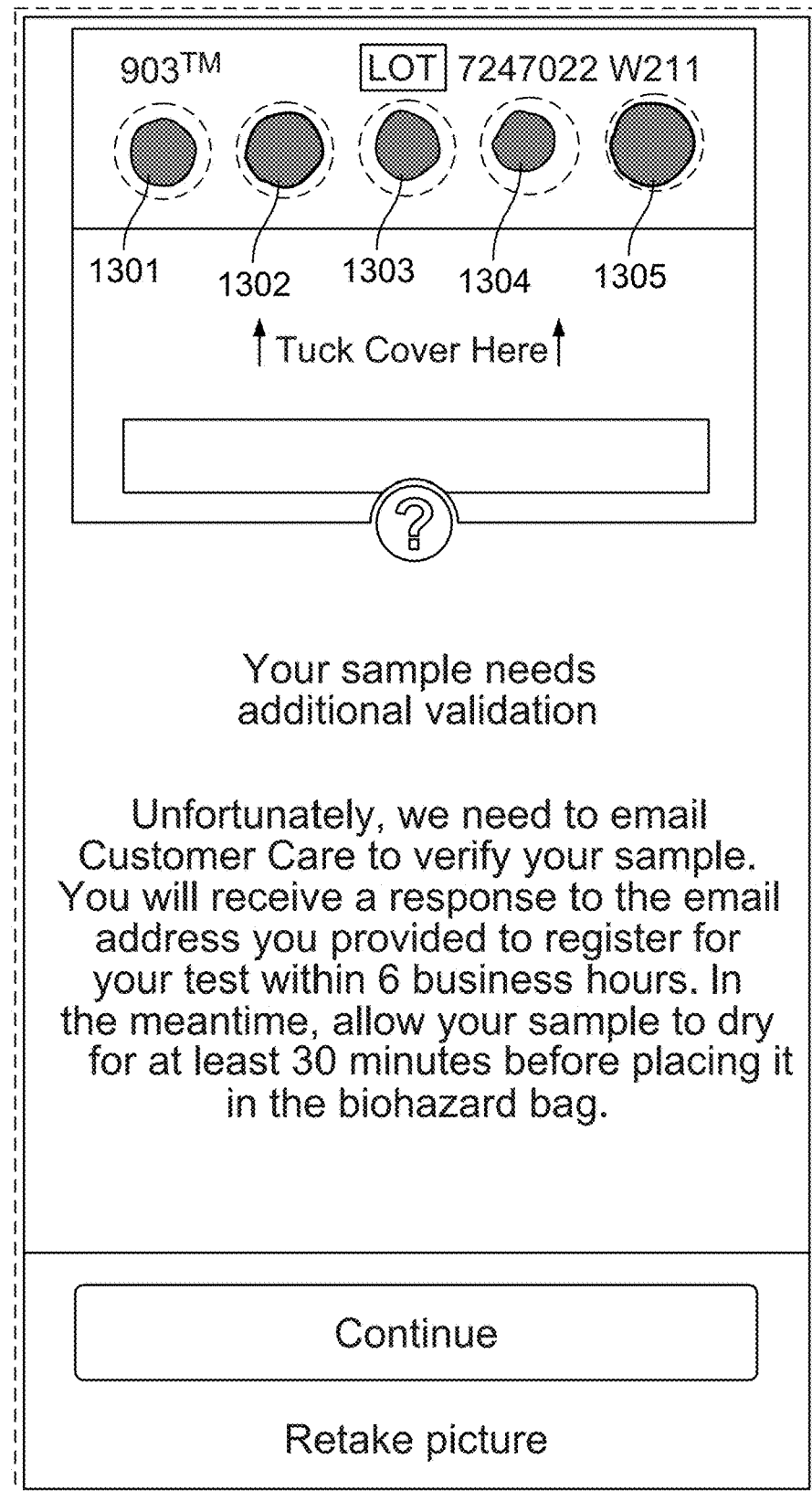
FIG. 13 illustrates an example of a notification for a sample collection device that was not validated in accordance with some embodiments.

In some embodiments, the test validation application does not validate the sample collection device after applying all of the image analysis algorithms to the image of the sample collection device. For example, the used sample collection device of FIG. 12 was not validated because there was not a sufficient amount of blood (e.g., less than a threshold amount) in a threshold number of sample collection areas. In response to not validating the used sample collection device, the test validation application may provide a notification to the user via the display associated with the electronic device. The notification may indicate that the used sample collection device needs additional validation. FIG. 13 provides an example of the notification 1300. In some embodiments, the test kit includes an additional sample collection device and the notification indicates that the user should perform an additional test using the additional sample collection device. The notification may indicate which of the fluid samples included an insufficient amount of fluid (e.g., samples 1301, 1303, 1304). The notification may also indicate which of the fluid samples included a sufficient amount of fluid (e.g., samples 1302, 1305). The notification may be color coded to indicate which of the fluid samples was sufficient or insufficient.

Figure 14:
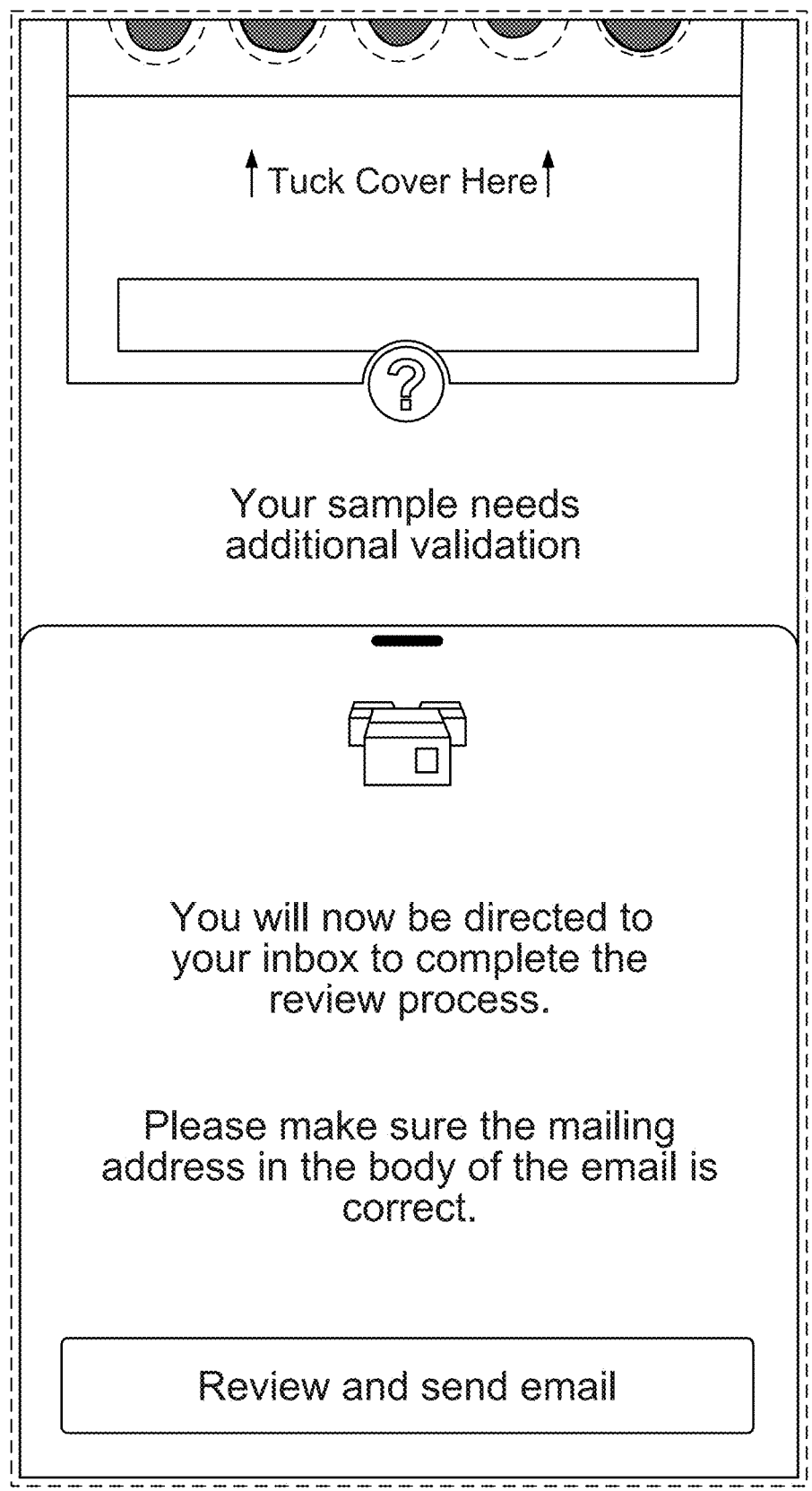
FIG. 14 illustrates an example of an interface that causes an email to be sent to the processing server in accordance with some embodiments.
Figure 15:
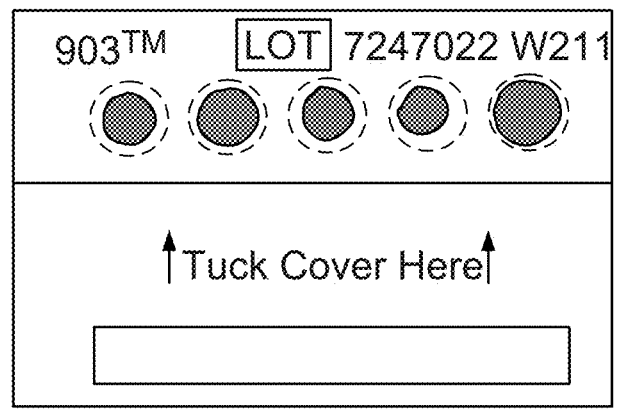
FIG. 15 illustrates an example of an email that is sent to the processing server in accordance with some embodiments.

Additional validation may include providing an email to a processing server. The test validation application may include an interface, as depicted in FIG. 14, that sends an email to the processing server. The email may include information associated with the user, information about the test kit associated with the sample collection device (e.g., test kit ID), as well as an image of the used sample collection device that was not validated. FIG. 15 illustrates an example of an email that is sent to the processing server.

FIG. 1 is a block diagram illustrating an embodiment of a system for validating a sample collection device. In the example shown, system 100 includes a user 101 associated with an electronic device 102. Electronic device 102 includes an image sensor (not shown) and test validation application 103.

Test validation application 103 is configured to display to the user one or more test kits associated with user 101 via a graphical user interface (GUI) associated with electronic device 102. User 101 provides to test validation application 103 via the GUI associated with electronic device 102 a selection of a test kit to validate. In response to receiving the selection, test validation application 103 is configured to provide to user 101 instructions describing how to validate a sample collection device 105 associated with the selected test kit via the display associated with electronic device 102. The instructions may indicate that user 101 should utilize the image sensor associated with electronic device 102 to capture an image of sample collection device 105 (e.g., the test kit includes one or more fluid samples associated with the user). A fluid sample may be a blood sample, a urine sample, a saliva solution, or other body fluid sample. The validation instructions may provide instructions describing how the sample collection device 105 is to be folded by user 101.

The image sensor associated with the electronic device is configured to capture an image of sample collection device 105 associated with the selected test kit and a processor of electronic device 102 is configured to analyze the captured image to determine whether the captured image is includes sample collection device 105. In some embodiments, the image is analyzed to determine if the image includes an object having a particular shape that corresponds to a shape of the sample collection device. The image may be analyzed to determine if the image includes an object having one or more particular characteristics associated with the sample collection device (e.g., a rectangular bar, a plurality of circles, a barcode, etc.). In response to a determination that the image does not include sample collection device 105, test validation application 103 requests for the user to capture an additional image. In response to a determination that the image is includes sample collection device 105, test validation application 103 analyzes the image utilizing one or more image analysis algorithms.

Test validation application 103 includes a plurality of image analysis algorithms to validate sample collection device 105. Test validation application 103 is configured to serially utilize the plurality of image analysis algorithms to validate sample collection device 105. In some embodiments, an image analysis algorithm is configured to determine whether there is a sufficient concentration of fluid included in a sample collection area of sample collection device 105. Sample collection device 105 is validated in response to a determination that user 101 has provided a sufficient amount of fluid to sample collection device 105 for later analysis at a processing facility. In some embodiments, test validation application 103 validates sample collection device 105 after applying a first algorithm of the plurality of image analysis algorithms to the image of sample collection device 105. In some embodiments, test validation application 103 validates sample collection device 105 after applying at least two of the image analysis algorithms to the image of sample collection device 105. In response to validating sample collection device 105, test validation application 103 may provide a notification to user 101 via the display associated with electronic device 102. The notification may indicate that sample collection device 105 has been validated (e.g., approved) and further handling instructions for sample collection device 105.

In some embodiments, test validation application 103 does not validate sample collection device 105 after applying all of the image analysis algorithms to the image of sample collection device 105. In response to not validating sample collection device 105, test validation application 103 may provide a notification to user 101 via the display associated with the electronic device 102. The notification may indicate that sample collection device 105 needs additional validation. In some embodiments, the test kit includes an additional sample collection device and the notification indicates that user 101 should perform an additional test using the additional sample collection device. The notification may indicate which of the fluid samples included an insufficient amount of fluid. The notification may also indicate which of the fluid samples included a sufficient amount of fluid. The notification may be color coded to indicate which of the fluid samples was sufficient or insufficient.

Additional validation may include providing an email to processing server 112 via connection 110. Connection 110 may be a wired or wireless connection. Connection 110 may be a local area network (LAN), a storage area network (SAN), a wide area network (WAN), a wireless local area network (WLAN), a campus area network (CAN), the Internet, an intranet, a cellular network, a virtual private network (VPN), a metropolitan area network (MAN), a personal area network (PAN), and/or a combination thereof.

Test validation application may include an interface, as depicted in FIG. 14, that sends an email to processing server 112. The email may include information associated with user 101, information about the test kit associated with sample collection device 105 (e.g., test kit ID), as well as an image of sample collection device 105 that was not validated.

Figure 2:
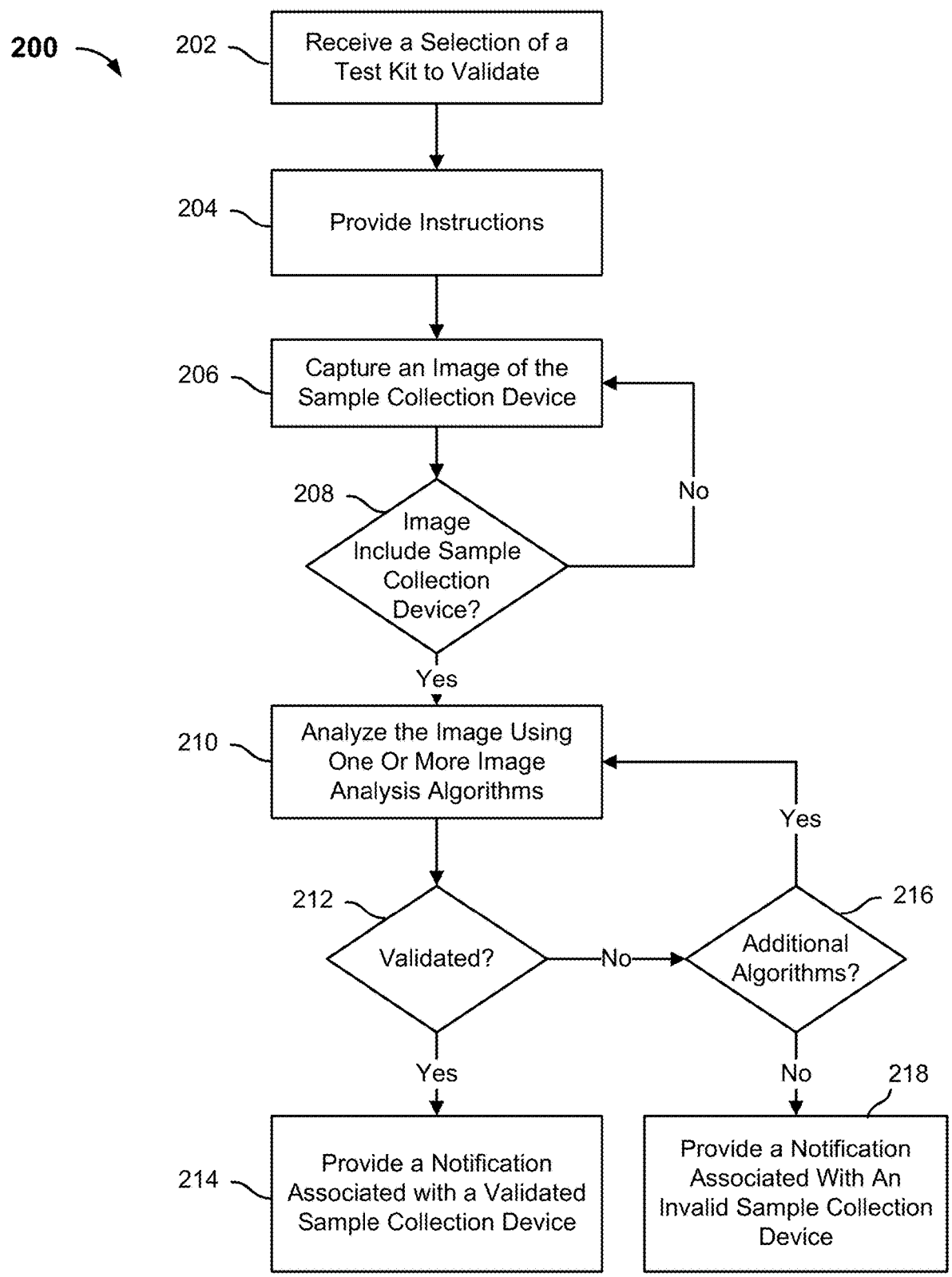
FIG. 2 is a flow diagram illustrating an example of a process for validating sample collection devices in accordance with some embodiments.

FIG. 2 is a flow diagram illustrating an example of a process for validating a sample collection device in accordance with some embodiments. In the example shown, process 200 may be implemented by a test validation application, such as test validation application 103.

At 202, a selection of a test kit to validate is received. One or more test kits may be registered to a user. An example of a test kit includes a food sensitivity test, a food allergy test, a celiac disease screening test, a metabolism test, a sexually transmitted disease test, etc.

At 204, instructions describing how to validate a sample collection device associated with the test kit are provided. The instructions may describe how to validate a sample collection device included in the test kit. The instructions may indicate that the user should utilize the camera associated with the electronic device to capture an image of a used sample collection device (e.g., the sample collection device includes one or more fluid samples associated with the user, a collection cassette, a collection card, etc.). In some embodiments, the validation instructions describe how the sample collection device is to be folded by the user.

At 206, an image of the sample collection device is captured.

At 208, it is determined whether the image includes the sample collection device. The image may be analyzed to determine if the image includes an object having a particular shape that corresponds to a shape of the sample collection device. The image may be analyzed to determine if the image includes an object having one or more particular characteristics associated with the sample collection device (e.g., rectangular bar, a plurality of circles, a barcode, etc.). In response to a determination that the image includes the sample collection device, process 200 proceeds to 210. In response to a determination that the image is deemed not to include the sample collection device, process 200 returns to 206 where the application request the user to capture an additional image.

In some embodiments, step 208 is optional.

At 210, the image of the sample collection device is analyzed using one or more image analysis algorithms. The test validation application includes a plurality of image analysis algorithms to validate the sample collection device. The test validation application may serially utilize the plurality of image analysis algorithms to validate the sample collection device. A sample collection device is validated in response to a determination that the user has provided a sufficient amount of fluid to the sample collection device for later analysis at a laboratory.

At 212, it is determined whether an analysis of the sample collection device has been validated using one of the one or more image analysis algorithms.

Figure 11:
FIG. 11 illustrates an example of a notification for a validated sample collection device in accordance with some embodiments.
Figure 17:
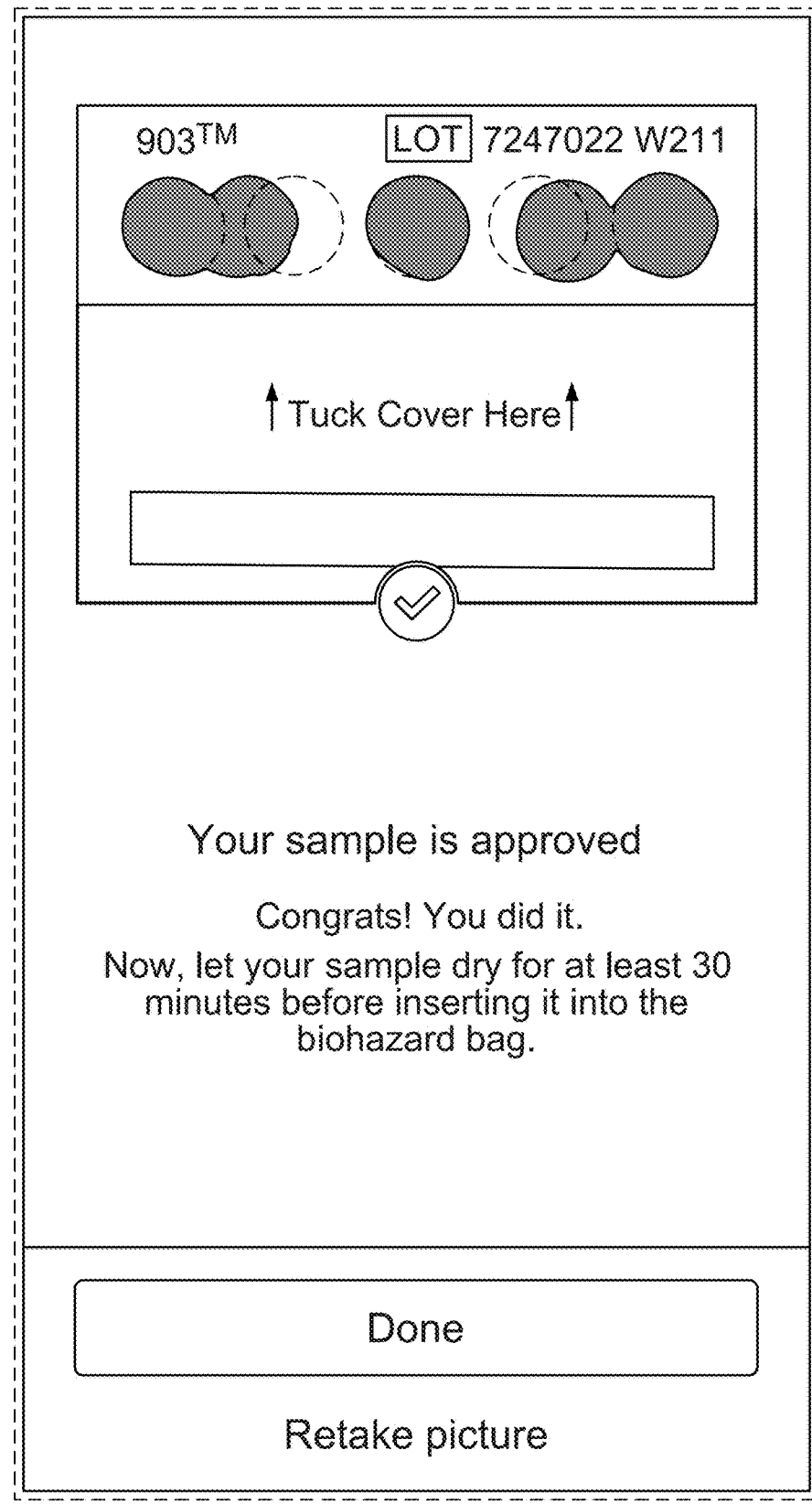
FIG. 17 illustrates an example of a notification for a validated sample collection device in accordance with some embodiments.

In response to a determination that the sample collection device has been validated using one of the one or more image analysis algorithms, process 200 proceeds to 214 where a notification associated with a validated sample collection device is provided. FIGS. 11 and 17 illustrates examples of notifications 1100, 1700 for a validated sample collection device.

In response to a determination that the sample collection device has not been validated using one of the one or more image analysis algorithms, process 200 proceeds to 216.

At 216, it is determined whether there is an additional image analysis algorithm to analyze the sample collection device image.

In response to a determination that there is an additional image analysis algorithm to analyze the sample collection device image, process 200 returns to step 210 where the sample collection device image is analyzed using the additional image analysis algorithm.

In response to a determination that there are no additional image analysis algorithms to analyze the sample collection device image, process 200 proceeds to step 218 where a notification associated with an invalid sample collection device is provided.

Figure 3:
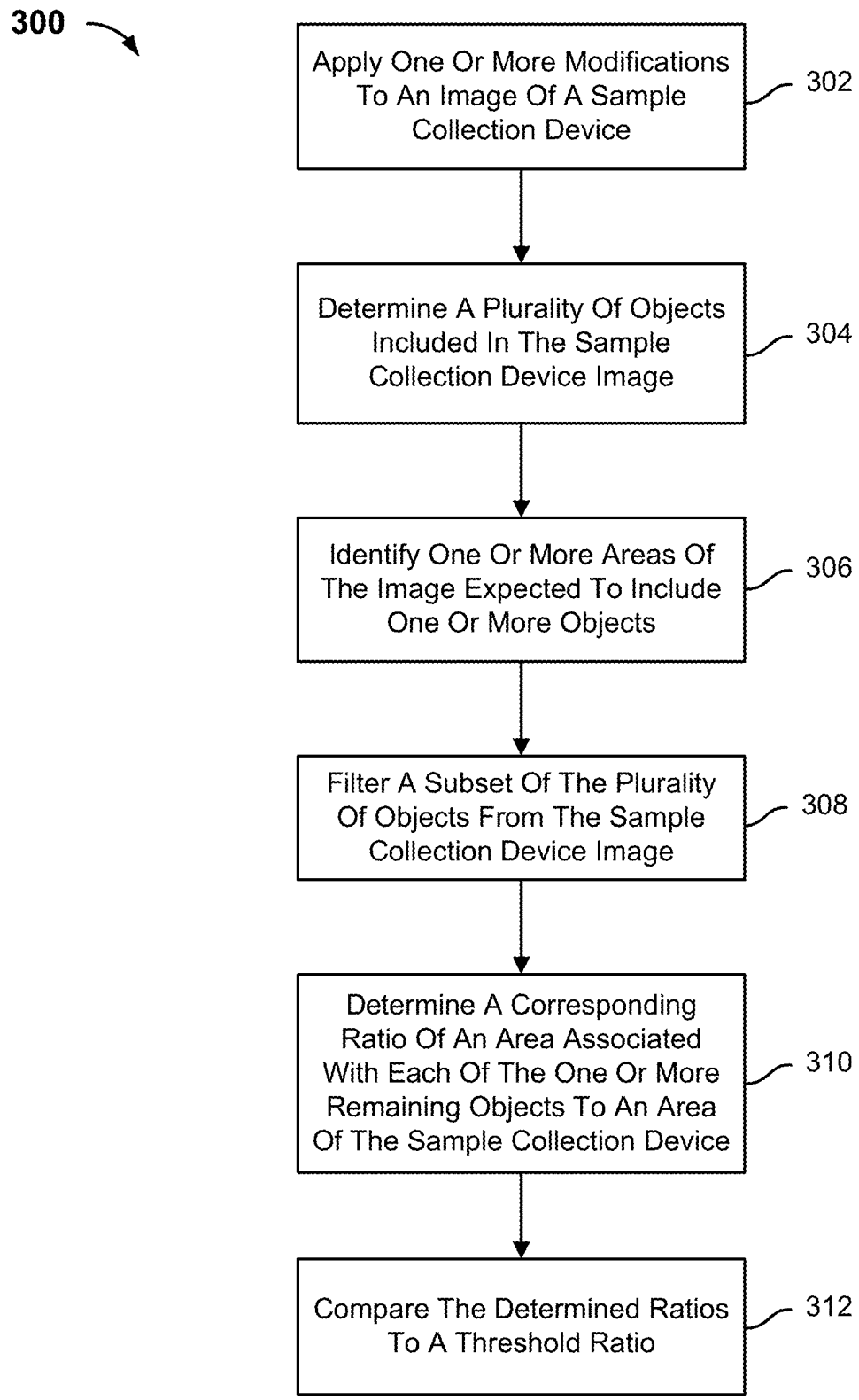
FIG. 3 is a flow diagram illustrating an example of a process for analyzing an image of a sample collection device in accordance with some embodiments.

FIG. 3 is a flow diagram illustrating an example of a process for analyzing an image of a sample collection device in accordance with some embodiments. In the example shown, process 300 may be implemented by a test validation application, such as test validation application 103. In some embodiments, process 300 is implemented to perform some or all of step 210 of process 200. In some embodiments, process 300 corresponds to a first image analysis algorithm utilized by the test validation application.

At 302, one or more modifications are applied to an image of a sample collection device. In some embodiments, the one or more modifications include cropping an image of the sample collection device from a captured image. In some embodiments, the one or more modifications include cropping the image of the sample collection device to a particular aspect ratio. In some embodiments, the one or more modifications include applying perspective correction to the image or cropped image of the sample collection device. Applying perspective correction may enable an area associated with a fluid sample on the sample collection device to be compared to a total area of the sample collection device. In some embodiments, the area associated with a fluid sample on the sample collection device is an individual area associated with a fluid sample. For example, the sample collection device may include one or more sample collection areas as illustrated in FIGS. 10, 12, and 16. The individual area associated with the fluid sample may correspond to the fluid sample included in one of the sample collection areas.

In some embodiments, white balance correction is applied to the image of the sample collection device to correct for lighting that might cause a background of the sample collection device to appear to be a non-white color (e.g., yellow).

In some embodiments, an aspect ratio of the sample collection device image is determined and compared to an expected aspect ratio of the sample collection device. The sample collection device image may be rotated in the event the determined aspect ratio of the sample collection device image does not match the expected aspect ratio of the sample collection device.

At 304, a plurality of objects included in the sample collection device image are determined. In some embodiments, the plurality of objects includes one or more lines, one or more shapes (e.g., circles, triangles, squares, rectangles, etc.) and/or one or more characters (e.g., letters, numbers, symbols, etc.).

At 306, one or more areas of the sample collection device image expected to include one or more objects are identified. A sample collection device may be expected to include one or more landmark objects. The one or more landmark objects may be identified (e.g., bar 1002 of FIG. 10). The one or more areas of the sample collection device image expected to include one or more objects may be a predetermined offset from the one or more identified landmark objects.

At 308, a subset of the plurality of objects is filtered from the sample collection device image. In some embodiments, the image analysis algorithm identifies one or more objects that are smaller than a first area threshold and filters the one or more identified objects from the image. For example, the image analysis algorithm may filter the text included in FIG. 10 from the image of the sample collection device.

In some embodiments, the image analysis algorithm identifies one or more objects that are larger than the first area threshold and a second area threshold and filters the one or more identified objects from the image. For example, the image analysis algorithm may filter the bar 1002 included in FIG. 10 from the image of the sample collection device.

The sample collection device image is a two-dimensional image. In some embodiments, the image analysis algorithm identifies one or more objects that are less than a first (x, y) coordinate and filters the one or more identified objects from the sample collection device image. In some embodiments, the image analysis algorithm identifies one or more objects that are greater than a second (x,y) coordinate and filters the one or more identified objects from the sample collection device image.

In some embodiments, the image analysis algorithm identifies one or more objects that have a width less than a first width threshold and filters the one or more identified objects from the sample collection device image. In some embodiments, the image analysis algorithm identifies one or more objects that have a width greater than the first width threshold and a second width threshold and filters the one or more identified objects from the sample collection device image.

In some embodiments, the image analysis algorithm identifies one or more objects that have a height less than a first height threshold and filters the one or more identified objects from the sample collection device image. In some embodiments, the image analysis algorithm identifies one or more objects that have a height greater than the first height threshold and a second height threshold and filters the one or more identified objects from the sample collection device image.

In some embodiments, one or more objects that are a threshold distance away from one or more areas of the image expected to include one or more objects are filtered from the image of the sample collection device.

At 310, a corresponding ratio of an area associated with each of the one or more remaining objects to an area of the sample collection device is determined. For example, a ratio of the area associated with object 1011 to the area of sample collection device 1004 may be determined, a ratio of the area associated with object 1012 to the area of sample collection device 1004 may be determined, a ratio of the area associated with object 1013 to the area of sample collection device 1004 may be determined, a ratio of the area associated with object 1014 to the area of sample collection device 1004 may be determined, and a ratio of the area associated with object 1015 to the area of sample collection device 1004 may be determined.

In another example, a ratio of the area associated with object 1211 to the area of sample collection device 1204 may be determined, a ratio of the area associated with object 1212 to the area of sample collection device 1204 may be determined, a ratio of the area associated with object 1213 to the area of sample collection device 1204 may be determined, a ratio of the area associated with object 1214 to the area of sample collection device 1204 may be determined, and a ratio of the area associated with object 1215 to the area of sample collection device 1204 may be determined.

At 312, the determined ratios are compared to a threshold ratio. The determined ratio may be rejected in the event the determined ratio is less than a threshold ratio. The determined ratio may be accepted in the event the determined ratio is greater than or equal to the threshold ratio.

The sample collection device may be rejected in the event a number of accepted ratios is less than a first accept threshold. The sample collection device may need additional validation in the event a number of accepted ratios is greater than or equal to the first accept threshold and less than a second accept threshold. The sample collection device may be validated in the event a number of accepted ratios is greater than the first accept threshold and greater than or equal to the second accept threshold.

Figure 4:
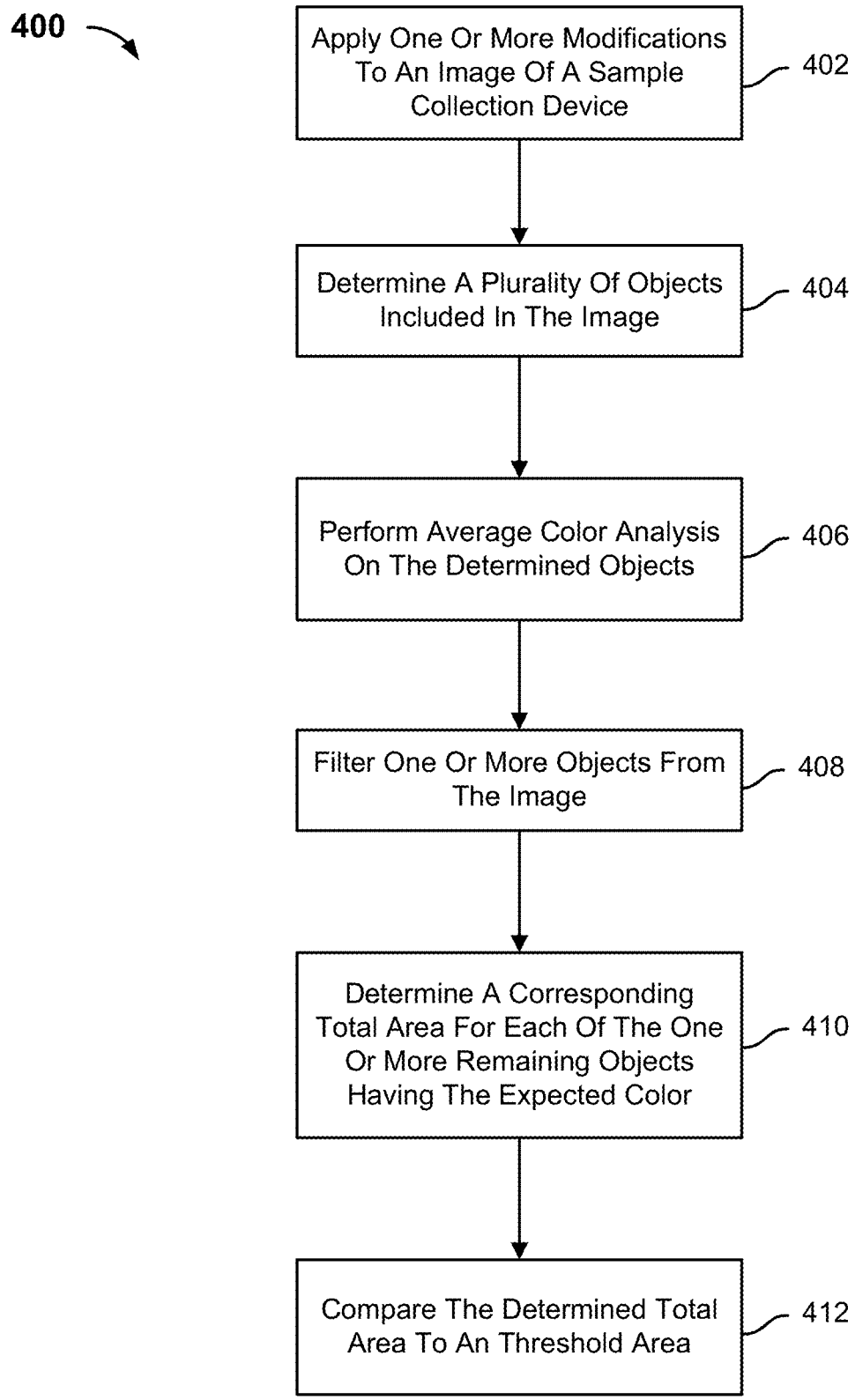
FIG. 4 is a flow diagram illustrating an example of a process for analyzing an image of a sample collection device in accordance with some embodiments.

FIG. 4 is a flow diagram illustrating an example of a process for analyzing an image of a sample collection device in accordance with some embodiments. In the example shown, process 400 may be implemented by a test validation application, such as test validation application 103. In some embodiments, process 400 is implemented to perform some or all of step 210 of process 200. In some embodiments, process 400 corresponds to one of the additional image analysis algorithms. In some embodiments, process 400 corresponds to a first image analysis algorithm.

A user may provide a plurality of fluid samples to the sample collection device but provide the plurality of fluid samples in a manner such that at least two of the plurality of fluid samples appear to be a single fluid sample. For example, the sample collection device 1604 of FIG. 16 illustrates a user providing fluid samples 1611, 1612, 1613, 1614, and 1615. Fluid samples 1611 and 1612 appear to be a single sample and fluid samples 1614 and 1615 also appear to be a single sample. Process 300 may result in a "reject" result or a "additional validation needed" result because the number of accepted objects is not greater than or equal to the second accept threshold. However, as seen in FIG. 16, the user may have provided a sufficient amount of fluid for later analysis at a processing facility.

At 402, one or more modifications are applied to an image of a sample collection device. In some embodiments, the one or more modifications include cropping an image of the sample collection device from a captured image. In some embodiments, the one or more modifications include cropping the image of the sample collection device to a particular aspect ratio. In some embodiments, the one or more modifications include applying perspective correction to the image or cropped image of the sample collection device.

In some embodiments, white balance correction is applied to the image of the sample collection device to correct for lighting that might cause a background of the sample collection device to appear to be a non-white color (e.g., yellow).

In some embodiments, an aspect ratio of the sample collection device image is determined and compared to an expected aspect ratio of the sample collection device. The sample collection device image may be rotated in the event the determined aspect ratio of the sample collection device image does not match the expected aspect ratio of the sample collection device.

At 404, a plurality of objects included in the captured image are determined. In some embodiments, the plurality of objects includes one or more lines, one or more shapes (e.g., circles, triangles, squares, rectangles, etc.) and/or one or more characters (e.g., letters, numbers, symbols, etc.).

At 406, an average color analysis is performed on the determined objects. An object to be analyzed is expected to have a particular color (e.g., a particular RGB value). An average color analysis is performed to determine an RGB color associated with each of the one or more determined objects.

At 408, one or more objects are filtered from the image. An object not having the expected color is filtered from the image. A first subset of the plurality of objects is filtered from the image of the sample collection device to produce a second subset of one or more remaining objects of the plurality of objects.

At 410, a corresponding total area for each of the one or more remaining objects having the expected color is determined.

At 412, the determined corresponding total area for each of the one or more remaining objects is compared to a threshold area. The sample collection device may be in the event the determined corresponding total area for none of the one or more remaining objects is greater than or equal to the threshold area. The sample collection device may be accepted in the event the determined corresponding total area for at least one of the one or more remaining objects is greater than or equal to the threshold area.

Figure 5:
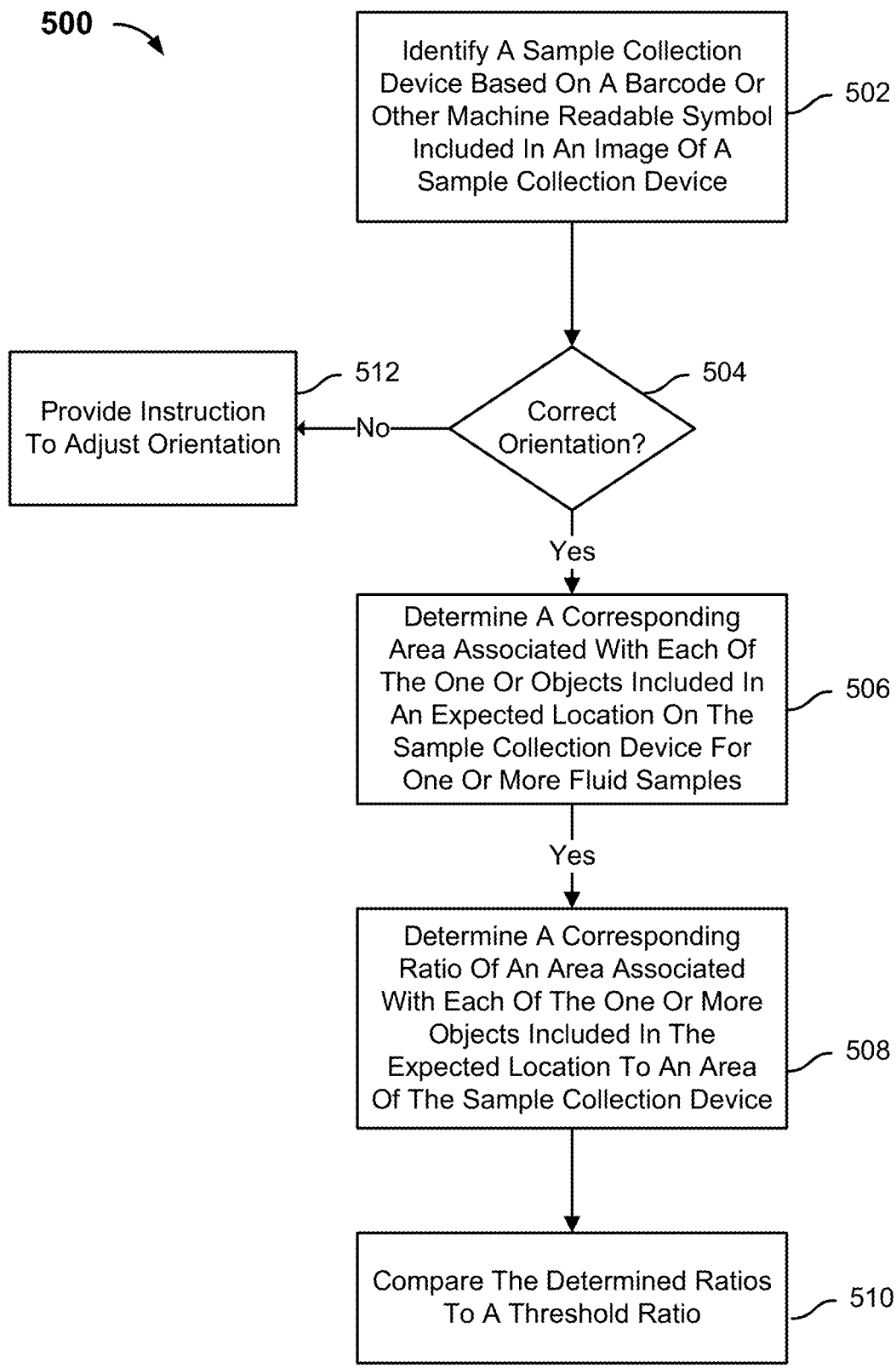
FIG. 5 is a flow diagram illustrating an example of a process for analyzing an image of a sample collection device in accordance with some embodiments.

FIG. 5 is a flow diagram illustrating an example of a process for analyzing an image of a sample collection device in accordance with some embodiments. In the example shown, process 500 may be implemented by a test validation application, such as test validation application 103. In some embodiments, process 500 is implemented to perform some or all of step 210 of process 200.

At 502, a sample collection device is identified based on a bar code or other machine-readable symbol included in an image of the sample collection device. In some embodiments, the sample collection card includes a bar code (e.g., linear bar code, matrix bar code). The bar code indicates information associated with the sample collection device. For example, the bar code may indicate the type of sample collection device, an expected location on the sample collection device for one or more fluid samples, an expected orientation of the sample collection device, a total area of the sample collection device, etc.

Different sample collection devices are associated with different bar codes or other machine-readable symbols. For example, the sample collection device may have 5, 10, 12, or any other number of expected sample areas. A sample collection device having 5 expected sample areas may be associated with a first bar code or other machine-readable symbol, a sample collection device having 10 expected sample areas may be associated with a second bar code or other machine-readable symbol, and a sample collection device having 12 expected sample areas may be associated with a third bar code or other machine-readable symbol.

At 504, it is determined whether the sample collection device is positioned in a correct orientation. In response to a determination that the card is positioned in the correct orientation, process 500 proceeds to 506. In response to a determination that the card is not positioned in the correct orientation, process 500 proceeds to 512.

At 506, a corresponding area associated with each of the one or more objects included in an expected location on the sample collection device for one or more fluid samples is determined.

At 508, a corresponding ratio of an area associated with each of the one or more objects included in the expected location to an area associated with the sample collection device is determined.

At 510, the determined ratios are compared to a threshold ratio. The determined ratio may be rejected in the event the determined ratio is less than a threshold ratio. The determined ratio may be accepted in the event the determined ratio is greater than or equal to the threshold ratio.

The sample collection device may be rejected in the event a number of accepted ratios is less than a first accept threshold. The sample collection device may need additional validation in the event a number of accepted ratios is greater than or equal to the first accept threshold and less than a second accept threshold. The sample collection device may be validated in the event a number of accepted ratios is greater than the first accept threshold and greater than or equal to the second accept threshold.

At 512, an instruction to adjust an orientation associated with the sample collection device is provided.

Figure 6:
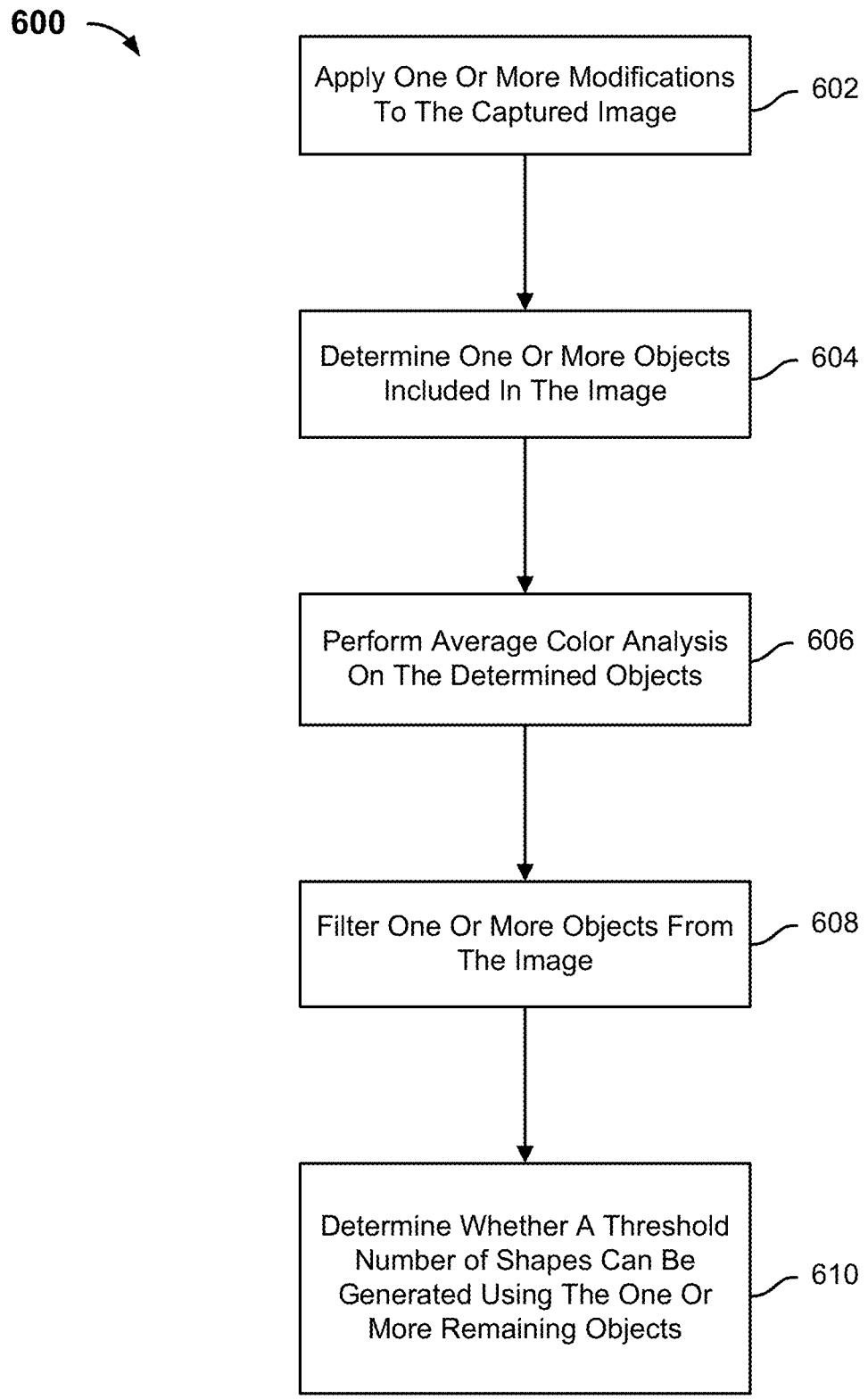
FIG. 6 is a flow diagram illustrating an example of a process for analyzing an image of a sample collection device in accordance with some embodiments.

FIG. 6 is a flow diagram illustrating an example of a process for analyzing an image of a sample collection device in accordance with some embodiments. In the example shown, process 600 may be implemented by a test validation application, such as test validation application 103. In some embodiments, process 600 is implemented to perform some or all of step 210 of process 200.

At 602, one or more modifications are applied to a captured image of a sample collection device. In some embodiments, the one or more modifications include cropping an image of the sample collection device from a captured image. In some embodiments, the one or more modifications include cropping the image of the sample collection device to a particular aspect ratio. In some embodiments, the one or more modifications include applying perspective correction to the image or cropped image of the sample collection device.

In some embodiments, white balance correction is applied to the image of the sample collection device to correct for lighting that might cause a background of the sample collection device to appear to be a non-white color (e.g., yellow).

In some embodiments, an aspect ratio of the sample collection device image is determined and compared to an expected aspect ratio of the sample collection device. The sample collection device image may be rotated in the event the determined aspect ratio of the sample collection device image does not match the expected aspect ratio of the sample collection device.

At 604, one or more objects included in the sample collection device image are determined. In some embodiments, the plurality of objects includes one or more lines, one or more shapes (e.g., circles, triangles, squares, rectangles, etc.) and/or one or more characters (e.g., letters, numbers, symbols, etc.).

At 606, an average color analysis is performed on the one or more determined objects. An object to be analyzed is expected to have a particular color (e.g., a particular RGB value). An average color analysis is performed to determine an RGB color associated with each of the one or more determined objects.

At 608, one or more objects are filtered from the sample collection device image. An object not having the expected color is filtered from the image. The sample collection device image includes one or more remaining objects.

At 610, it is determined whether a threshold number of predetermined shapes can be generated using the one or more remaining objects. An example of a predetermined shape is a circle having a particular radius or diameter. In some embodiments, the sample collection device is rejected in the event the threshold number of predetermined shapes (e.g., 4) cannot be generated using the one or more remaining objects. In some embodiments, the sample collection device is accepted in the event the threshold number of predetermined shapes can be generated using the one or more remaining objects.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
capturing an image of a sample collection device;
analyzing the image of the sample collection device to determine whether the sample collection device includes a sufficient amount of fluid sample including by utilizing a first image analysis algorithm to determine an area of the fluid sample in the image of the sample collection device;
validating the image of the sample collection device based on a result of the image analysis, wherein validating the image based on the result of the image analysis includes validating the image based on a result of the first image analysis algorithm; and
in response to the sample collection device not being validated as a result of utilizing the first image analysis algorithm, analyzing the image of the sample collection device including by utilizing one or more other image analysis algorithms, wherein analyzing the image of the sample collection device utilizing the one or more other image analysis algorithms includes:
determining a plurality of objects included in the image; and
performing an average color analysis on the one or more determined objects.

2. The method of claim 1, wherein the sample collection device includes one or more locations at which the fluid sample is to be provided.

3. The method of claim 1, wherein utilizing the first image analysis algorithm includes applying one or more modifications to the image of the sample collection device.

4. The method of claim 3, wherein the one or more modifications includes applying perspective correction to the image of the sample collection device.

5. The method of claim 3, wherein utilizing the first image analysis algorithm further includes:
determining a plurality of objects included in the image of the sample collection device;
identifying one or more areas of the image expected to include one or more objects; and
filtering a first subset of the plurality of objects from the image of the sample collection device to produce a second subset of one or more remaining objects of the plurality of objects.

6. The method of claim 5, wherein utilizing the first image analysis algorithm further includes determining a corresponding ratio of an area associated with each of the one or more remaining objects to an area of the sample collection device.

7. The method of claim 6, wherein utilizing the first image analysis algorithm further includes comparing the determined ratios to a threshold ratio, wherein the image of the sample collection device is validated based on the comparison of the determined ratios to the threshold ratio.

8. The method of claim 1, wherein analyzing the image of the sample collection device utilizing one or more other image analysis algorithms further includes:
filtering, based on a result of the average color analysis, a first subset of the plurality of objects from the image of the sample collection device to produce a second subset of one or more remaining objects of the plurality of objects.

9. The method of claim 8, wherein analyzing the image of the sample collection device utilizing one or more other image analysis algorithms further includes:
determining a corresponding total area for each of the one or more remaining objects; and
comparing the corresponding determined total area for each of the one or more remaining objects to a threshold area, wherein the image of the sample collection device is validated based on the comparison of the determined total areas to the threshold area.

10. The method of claim 8, wherein analyzing the image of the sample collection device utilizing one or more other image analysis algorithms further includes determining whether a threshold number of predetermined shapes can be generated using the one or more remaining objects.

11. The method of claim 10, wherein the image of the sample collection device is validated based on whether the threshold number of predetermined shapes can be generated using the one or more remaining objects.

12. A method, comprising:
capturing an image of a sample collection device;
analyzing the image of the sample collection device to determine whether the sample collection device includes a sufficient amount of fluid sample including by utilizing a first image analysis algorithm to determine an area of the fluid sample in the image of the sample collection device;
validating the image of the sample collection device based on a result of the image analysis, wherein validating the image based on the result of the image analysis includes validating the image based on a result of the first image analysis algorithm; and
in response to the sample collection device not being validated as a result of utilizing the first image analysis algorithm, analyzing the image of the sample collection device including by utilizing one or more other image analysis algorithms, wherein analyzing the image of the sample collection device utilizing one or more other image analysis algorithms further includes:
scanning a barcode or other machine-readable symbol associated with the sample collection device; and
identifying the sample collection device based on the scanned barcode or other machine-readable symbol, wherein the scanned barcode or other machine-readable symbol indicates an expected location for one or more fluid samples associated with the sample collection device.

13. The method of claim 12, wherein analyzing the image of the sample collection device utilizing one or more other image analysis algorithms further includes:
determining a corresponding area associated with each of one or more objects included in the expected location for the one or more fluid samples associated with the sample collection device; and
determining a corresponding ratio of the determined corresponding area associated with each of the one or more objects included in the expected location to an area of sample collection device.

14. The method of claim 13, wherein analyzing the image of the sample collection device utilizing one or more other image analysis algorithms further includes comparing the determined ratios to a threshold ratio, wherein the image of the sample collection device is validated based on the comparison of the determined ratios to the threshold ratio.

15. A system, comprising:
an image sensor configured to capture an image of a sample collection device; and
a processor configured to:
analyze the image of the sample collection device to determine whether the sample collection device includes a sufficient amount of fluid sample including by utilizing a first image analysis algorithm to determine an area of the fluid sample in the image of the sample collection device;
validate the image of the sample collection device based on a result of the image analysis, wherein validating the image based on the result of the image analysis includes validating the image based on a result of the first image analysis algorithm; and
in response to the sample collection device not being validated as a result of utilizing the first image analysis algorithm, analyze the image of the sample collection device including by utilizing one or more other image analysis algorithms, wherein analyzing the image of the sample collection device utilizing the one or more other image analysis algorithms includes:
determining a plurality of objects included in the image; and
performing an average color analysis on the one or more determined objects.

16. The system of claim 15, wherein the sample collection device includes one or more locations at which the fluid sample is to be provided.

17. The system of claim 15, wherein utilizing the first image analysis algorithm includes applying one or more modifications to the image of the sample collection device.

18. The system of claim 17, wherein the one or more modifications includes applying perspective correction to the image of the sample collection device.

19. The system of claim 17, wherein utilizing the first image analysis algorithm further includes:
determining a plurality of objects included in the image of the sample collection device;
identifying one or more areas of the image expected to include one or more objects; and
filtering a first subset of the plurality of objects from the image of the sample collection device to produce a second subset of one or more remaining objects of the plurality of objects.

20. The system of claim 19, wherein utilizing the first image analysis algorithm further includes determining a corresponding ratio of an area associated with each of the one or more remaining objects to an area of the sample collection device.

21. The system of claim 20, wherein utilizing the first image analysis algorithm further includes comparing the determined ratios to a threshold ratio, wherein the image of the sample collection device is validated based on the comparison of the determined ratios to the threshold ratio.

22. A computer program product embodied in a non-transitory computer readable medium and comprising computer instructions for:
   capturing an image of a sample collection device;
   analyzing the image of the sample collection device to determine whether the sample collection device includes a sufficient amount of fluid sample including by utilizing a first image analysis algorithm to determine an area of the fluid sample in the image of the sample collection device;
   validating the image of the sample collection device based on a result of the image analysis, wherein validating the image based on the result of the image analysis includes validating the image based on a result of the first image analysis algorithm; and
   in response to the sample collection device not being validated as a result of utilizing the first image analysis algorithm, analyzing the image of the sample collection device including by utilizing one or more other image analysis algorithms, wherein analyzing the image of the sample collection device utilizing the one or more other image analysis algorithms includes:
      determining a plurality of objects included in the image; and
      performing an average color analysis on the one or more determined objects.

23. The computer program product of claim 22, wherein the sample collection device includes one or more locations at which the fluid sample is to be provided.

24. The computer program product of claim 22, wherein utilizing the first image analysis algorithm includes applying one or more modifications to the image of the sample collection device.

25. The computer program product of claim 24, wherein the one or more modifications includes applying perspective correction to the image of the sample collection device.

26. The computer program product of claim 24, wherein utilizing the first image analysis algorithm further includes:
   determining a plurality of objects included in the image of the sample collection device;
   identifying one or more areas of the image expected to include one or more objects; and
   filtering a first subset of the plurality of objects from the image of the sample collection device to produce a second subset of one or more remaining objects of the plurality of objects.

27. The computer program product of claim 26, wherein utilizing the first image analysis algorithm further includes determining a corresponding ratio of an area associated with each of the one or more remaining objects to an area of the sample collection device.

28. The computer program product of claim 27, wherein utilizing the first image analysis algorithm further includes comparing the determined ratios to a threshold ratio, wherein the image of the sample collection device is validated based on the comparison of the determined ratios to the threshold ratio.

29. A system, comprising:
   an image sensor configured to capture an image of a sample collection device; and
   a processor configured to:
      analyze the image of the sample collection device to determine whether the sample collection device includes a sufficient amount of fluid sample including by utilizing a first image analysis algorithm to determine an area of the fluid sample in the image of the sample collection device;
      validate the image of the sample collection device based on a result of the image analysis, wherein validating the image based on the result of the image analysis includes validating the image based on a result of the first image analysis algorithm; and
      in response to the sample collection device not being validated as a result of utilizing the first image analysis algorithm, analyze the image of the sample collection device including by utilizing one or more other image analysis algorithms, wherein analyzing the image of the sample collection device utilizing one or more other image analysis algorithms further includes:
         scanning a barcode or other machine-readable symbol associated with the sample collection device; and
         identifying the sample collection device based on the scanned barcode or other machine-readable symbol, wherein the scanned barcode or other machine-readable symbol indicates an expected location for one or more fluid samples associated with the sample collection device.

30. The system of claim 29, wherein analyzing the image of the sample collection device utilizing one or more other image analysis algorithms further includes:
   determining a corresponding area associated with each of one or more objects included in the expected location for the one or more fluid samples associated with the sample collection device; and
   determining a corresponding ratio of the determined corresponding area associated with each of the one or more objects included in the expected location to an area of sample collection device.

31. The system of claim 30, wherein analyzing the image of the sample collection device utilizing one or more other image analysis algorithms further includes comparing the determined ratios to a threshold ratio, wherein the image of the sample collection device is validated based on the comparison of the determined ratios to the threshold ratio.

32. A computer program product embodied in a non-transitory computer readable medium and comprising computer instructions for:
   capturing an image of a sample collection device;
   analyzing the image of the sample collection device to determine whether the sample collection device includes a sufficient amount of fluid sample including by utilizing a first image analysis algorithm to determine an area of the fluid sample in the image of the sample collection device;
   validating the image of the sample collection device based on a result of the image analysis, wherein validating the image based on the result of the image analysis includes validating the image based on a result of the first image analysis algorithm; and
   in response to the sample collection device not being validated as a result of utilizing the first image analysis algorithm, analyzing the image of the sample collection device including by utilizing one or more other image analysis algorithms, wherein analyzing the image of the sample collection device utilizing one or more other image analysis algorithms further includes:
      scanning a barcode or other machine-readable symbol associated with the sample collection device; and identifying the sample collection device based on the scanned barcode or other machine-readable symbol, wherein the scanned barcode or other machine-readable symbol indicates an expected location for one or more fluid samples associated with the sample collection device.

33. The computer program product of claim 32, wherein analyzing the image of the sample collection device utilizing one or more other image analysis algorithms further includes:
   determining a corresponding area associated with each of one or more objects included in the expected location for the one or more fluid samples associated with the sample collection device; and
   determining a corresponding ratio of the determined corresponding area associated with each of the one or more objects included in the expected location to an area of sample collection device.

34. The computer program product of claim 33, wherein analyzing the image of the sample collection device utilizing one or more other image analysis algorithms further includes comparing the determined ratios to a threshold ratio, wherein the image of the sample collection device is validated based on the comparison of the determined ratios to the threshold ratio.

* * * * *